United States Patent
Kang et al.

(10) Patent No.: US 6,737,277 B1
(45) Date of Patent: *May 18, 2004

(54) IMMUNOASSAY DEVICES AND MATERIALS

(75) Inventors: Jemo Kang, Princeton, NJ (US); Byungwoo Youn, Wyckoff, NJ (US); Young Ho Oh, Edison, NJ (US)

(73) Assignee: PMB-Selfcare LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/599,499

(22) Filed: Jun. 23, 2000

Related U.S. Application Data

(62) Division of application No. 09/263,884, filed on Mar. 8, 1999, now Pat. No. 6,506,612, which is a division of application No. 08/970,425, filed on Nov. 14, 1997, now Pat. No. 6,027,943, which is a division of application No. 08/659,937, filed on Jun. 7, 1996, now Pat. No. 5,728,587, which is a continuation of application No. 08/070,803, filed on Jun. 3, 1993, now Pat. No. 5,559,041, which is a division of application No. 07/456,982, filed on Dec. 18, 1989, now Pat. No. 5,252,496.

(51) Int. Cl.[7] .............................................. G01N 33/558
(52) U.S. Cl. .......................... 436/514; 422/56; 422/57; 422/58; 422/61; 435/7.92; 435/7.93; 435/7.94; 435/7.95; 435/287.1; 435/287.2; 435/287.7; 435/287.9; 435/970; 435/805; 435/810; 436/164; 436/169; 436/518; 436/524; 436/529; 436/530; 436/805; 436/810
(58) Field of Search ................................ 422/56–58, 61; 435/7.91–7.95, 287.1, 287.2, 287.7, 287.9, 970, 805, 810; 436/164, 169, 514, 518, 524, 529, 530, 805, 810

(56) References Cited

U.S. PATENT DOCUMENTS

| | | |
|---|---|---|
| 4,090,888 A | 5/1978 | Rademachers et al. |
| 4,168,146 A | 9/1979 | Grubb et al. |
| 4,253,844 A | 3/1981 | Limet et al. |
| 4,254,096 A | 3/1981 | Monthony et al. |
| 4,313,734 A | 2/1982 | Leuvering |

(List continued on next page.)

FOREIGN PATENT DOCUMENTS

| | | |
|---|---|---|
| EP | 0125118 | 11/1984 |
| EP | 0143574 | 6/1985 |
| EP | 0164194 | 12/1985 |
| EP | 0186100 | 7/1986 |
| EP | 0191640 | 8/1986 |

(List continued on next page.)

OTHER PUBLICATIONS

Kenn et al. (1985) Methods for Reducing non–specific . . . , J. Immunol. Meth. 85:409–419.
Colowick et al. (1972) Methods in Enzymology XXVI(c); pp. 28–42.

*Primary Examiner*—Christopher L. Chin
(74) *Attorney, Agent, or Firm*—Birch, Stewart, Kolasch & Birch, LLP

(57) ABSTRACT

An immunochemical assay device comprising a base member, an array disposed on the base member, and at least one assay indicia zone. The array comprises (i) a reservoir pad to receive sample liquid, (ii) a wicking membrane, and (iii) at least one filter zone interposed between the wicking membrane and the reservoir pad. The filter zone being operable to permit passage of any specific immunocomplex to the wicking membrane while impeding passage of larger components.

26 Claims, 2 Drawing Sheets

U.S. PATENT DOCUMENTS

| | | |
|---|---|---|
| 4,315,907 A | 2/1982 | Fridlender et al. |
| 4,318,707 A | 3/1982 | Litman et al. |
| 4,332,788 A | 6/1982 | Mochida et al. |
| 4,361,537 A | 11/1982 | Deutsch et al. |
| 4,366,241 A | 12/1982 | Tom et al. |
| 4,373,932 A | 2/1983 | Gribnau et al. |
| 4,415,700 A | 11/1983 | Batz et al. |
| 4,435,504 A | 3/1984 | Zuk et al. |
| 4,446,232 A | 5/1984 | Liotta |
| 4,472,498 A | 9/1984 | Masuda et al. |
| 4,514,508 A | 4/1985 | Hirschfeld |
| 4,595,656 A | 6/1986 | Allen et al. |
| 4,632,901 A | 12/1986 | Valkirs |
| 4,703,017 A | 10/1987 | Campbell et al. |
| 4,757,004 A | 7/1988 | Houts et al. |
| 4,770,853 A | 9/1988 | Bernstein |
| 4,780,422 A | 10/1988 | Mitani et al. |
| 4,786,589 A | 11/1988 | Rounds |
| 4,786,594 A | 11/1988 | Khanna et al. |
| 4,786,606 A | 11/1988 | Geigel et al. |
| 4,790,979 A | 12/1988 | Terminiello et al. |
| 4,853,335 A | 8/1989 | Olsen et al. |
| 4,857,453 A | 8/1989 | Ullman et al. |
| 4,859,612 A | 8/1989 | Cole et al. |
| 4,861,711 A | 8/1989 | Friesen et al. |
| 4,870,005 A | 9/1989 | Akiyoshi et al. |
| 4,900,663 A | 2/1990 | Wie et al. |
| 4,943,522 A | 7/1990 | Eisinger et al. |
| 4,956,275 A | 9/1990 | Zuk et al. |
| 4,956,302 A | 9/1990 | Gordon et al. |
| 4,959,305 A | 9/1990 | Woodrum |
| 4,960,691 A | 10/1990 | Gordon et al. |
| 5,030,558 A | 7/1991 | Litman et al. |
| 5,073,484 A | 12/1991 | Swanson et al. |
| 5,075,078 A | 12/1991 | Osikowicz et al. |
| 5,079,142 A | 1/1992 | Coleman et al. |
| 5,085,987 A | 2/1992 | Olson |
| 5,085,988 A | 2/1992 | Olson |
| 5,096,833 A | 3/1992 | Lau et al. |
| 5,120,643 A | 6/1992 | Ching et al. |
| 5,141,850 A | 8/1992 | Cole et al. |
| 5,141,875 A | 8/1992 | Kelton et al. |
| 5,156,952 A | 10/1992 | Litman et al. |
| 5,156,953 A | 10/1992 | Litman et al. |
| 5,158,869 A | 10/1992 | Pouletty et al. |
| 5,166,051 A | 11/1992 | Killeen et al. |
| 5,188,938 A | 2/1993 | Khanna et al. |
| 5,206,177 A | 4/1993 | DeLaCroix et al. |
| 5,212,065 A | 5/1993 | Pegg et al. |
| 5,232,835 A | 8/1993 | Litman et al. |
| 5,258,163 A | 11/1993 | Krause et al. |
| 5,260,193 A | 11/1993 | Olson |
| 5,354,692 A | 10/1994 | Yang et al. |
| 5,514,602 A | 5/1996 | Brooks et al. |
| 5,559,041 A * | 9/1996 | Kang et al. ............ 436/518 |
| 5,591,164 A | 1/1997 | Nazre et al. |
| 5,591,645 A | 1/1997 | Rosenstein |
| 5,602,040 A | 2/1997 | May et al. |
| 5,625,871 A | 4/1997 | Myer et al. |
| 5,654,162 A | 8/1997 | Guire et al. |
| 5,656,503 A | 8/1997 | May et al. |
| 5,714,389 A | 2/1998 | Charlton et al. |
| 5,728,587 A * | 3/1998 | Kang et al. ............ 436/518 |
| 5,989,921 A | 11/1999 | Charlton et al. |
| 6,027,943 A * | 2/2000 | Kang et al. ............ 436/518 |

FOREIGN PATENT DOCUMENTS

| | | |
|---|---|---|
| EP | 0202081 | 11/1986 |
| EP | 0100619 | 12/1986 |
| EP | 0212599 A2 | 4/1987 |
| EP | 0250137 | 12/1987 |
| EP | 0279097 | 8/1988 |
| EP | 0280559 | 8/1988 |
| EP | 0282192 | 9/1988 |
| EP | 0284232 | 9/1988 |
| EP | 0 291 194 | * 11/1988 |
| EP | 0296724 | 12/1988 |
| EP | 0298368 | 1/1989 |
| EP | 0299359 | 1/1989 |
| EP | 0299428 | 1/1989 |
| EP | 0305536 | 3/1989 |
| EP | 0306336 | 3/1989 |
| EP | 0306772 | 3/1989 |
| EP | 0309992 | 4/1989 |
| EP | 0323605 A2 | 7/1989 |
| EP | 0323605 A2 | 12/1989 |
| EP | 0383619 B1 | 8/1990 |
| EP | 0383619 A1 | 8/1990 |
| GB | 2204398 | 11/1988 |
| WO | WO8603839 | 7/1986 |
| WO | WO 88/08534 | * 11/1988 |
| WO | 81085348 | 11/1988 |
| WO | 88108534 | 11/1988 |
| WO | 88108536 | 11/1988 |
| WO | 88109824 | 12/1988 |
| WO | 89103044 | 4/1989 |
| WO | WO 9009592 | 8/1990 |

* cited by examiner

IMMUNOASSAY DEVICES AND MATERIALS

This application is a divisional of application Ser. No. 09/263,884, filed on Mar. 8, 1999, now U.S. Pat. No. 6,506,612 (which is a divisional of Ser. No. 08/970,425, U.S. Pat. No. 6,027,943, filed on Nov. 14, 1997, which is a Rule 60 divisional of Ser. No. 08/659,937, U.S. Pat. No. 5,728,587, filed Jun. 7, 1996, which is a Rule 60 continuation of Ser. No. 08/070,803, U.S. Pat. No. 5,559,041 filed Jun. 3, 1993; which is a Rule 60 divisional of Ser. No. 07/456,982, U.S. Pat. No. 5,252,496, filed Dec. 18, 1989, the entire contents of which are hereby incorporated by reference.

BACKGROUND OF THE INVENTION

Various methods for detecting the presence of an analyte in a sample of biological fluid through the use of immunochemistry have been described. In the so-called "sandwich" method, for example, a target analyte such as an antigen is "sandwiched" between a labeled antibody and an antibody immobilized onto a solid support. The assay is read by observing the presence and amount of bound antigen-labeled antibody complex. In the competition immunoassay method, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other methods discussed below can detect both antibodies and antigens, they are generally referred to as immunochemical ligand-receptor assays or simply immunoassays.

Solid phase immunoassay devices, whether sandwich or competition type, provide sensitive detection of an analyte in a biological fluid sample such as blood or urine. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. More recently, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

In the more common forms of dipstick assays, as typified by home pregnancy and ovulation detection kits, immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution. Baxter et al., EP-A 0 125 118, disclose such a sandwich type dipstick immunoassay. Kali et al., EP-A 0 282 192, disclose a dipstick device for use in competition type assays.

Flow-through type immunoassay devices were designed to obviate the need for extensive incubation and cumbersome washing steps associated with dipstick assays. Valkirs et al., U.S. Pat. No. 4,632,901, disclose a device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

The requirement of multiple addition and washing steps with dipstick and flow-through type immunoassay devices increases the likelihood that minimally trained personnel and home users will obtain erroneous assay results.

In migration type assays, a membrane is impregnated with the reagents needed to perform the assay. An analyte detection zone is provided in which labeled analyte is bound and assay indicia is read. See, for example, Tom et al., U.S. Pat. No. 4,366,241, and Zuk, EP-A 0 143 574.

The sensitivity of migration type assays is frequently reduced, however, by the presence or formation in the sample of undesirable solid components which block the passage of labeled analyte to the detection zone. Assay sensitivity also declines when migration assay devices are flooded with too much liquid sample.

Migration assay devices usually incorporate within them reagents which have been attached to colored labels, thereby permitting visible detection of the assay results without addition of further substances. See, for example, Bernstein, U.S. Pat. No. 4,770,853, May et al., WO 88/08534, and Ching et al., EP-A 0 299 428.

Among such labels are gold sol particles such as those described by Leuvering in U.S. Pat. No. 4,313,734, dye sol particles such as described by Gribnau et al., in U.S. Pat. No. 4,373,932 and May et al., WO 88/08534, dyed latex such as described by May, supra, Snyder, EP-A 0 280 559 and 0 281 327, and dyes encapsulated in liposomes by Campbell et al., U.S. Pat. No. 4,703,017. These colored labels are generally limited in terms of the immobilization methods which are suitable. Moreover, they require a relatively large amount of ligand molecule and can involve expensive reagents, thereby adding to the cost.

DETAILED DESCRIPTION

The present invention comprises a device for detection of the presence of an analyte in a sample of biological fluid through the use of immunochemical ligand-receptor reactions and specially selected, treated, and arranged filter materials. The nature of the invention will be apparent from the following description and from the accompanying drawings in which.

Figure 1:
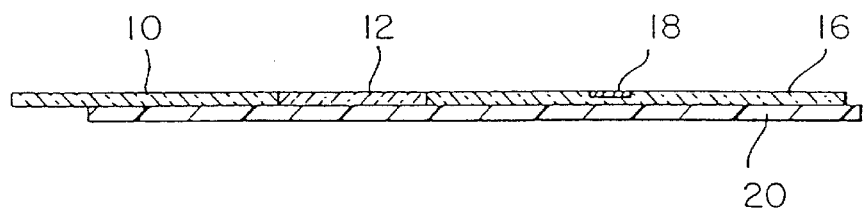
FIG. 1 is a cross sectional view of a typical unidirectional assay device.

Referring now to FIG. 1, reservoir pad 10, filter element 12, and wicking membrane 16, which contains immobilized substance defined in assay indicia zone 18, are disposed on base 20. Reservoir pad 10 has sufficient porosity and volume to receive and contain a liquid sample on which the assay is to be performed. Filter element 12 is adjacent to and contiguous across a relatively small surface of reservoir pad 10 relative to the volume of pad 10 so as to meter the passage of the liquid sample emerging from reservoir pad 10 into filter element 12.

Disposed in defined zone 18 of wicking membrane 16 is an immobilized substance which is operable to bind any specific ligand receptor complexes contained in the sample passing through filter element 12.

In this embodiment, a reagent operable to produce a specific ligand receptor complex is added to the sample where it will react to form the complex (assuming it contains the appropriate analyte) and the sample then brought into contact with reservoir pad 10. The sample migrates through filter element 12 where any unwanted components which may be present in the sample become trapped, and on into wicking membrane 16. Labeled analyte if present binds to assay indicia zone 18 producing a visibly detectable signal.

Figure 2:
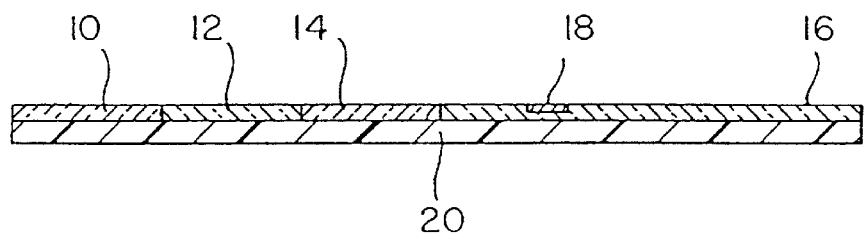
FIG. 2 is a cross sectional view of a second embodiment of a unidirectional assay device.

In the embodiment shown in FIG. 2, there is present, in addition to reservoir pad 10, filter element 12, and wicking membrane 16, second filter element 14 which is disposed on base 20. Reservoir pad 10 has sufficient porosity and volume to receive and contain a liquid sample on which the assay is to be performed. First filter element 12 is adjacent to and contiguous across a relatively small surface of reservoir pad 10 relative to the volume of pad 10 so as to meter the passage of the liquid sample emerging from reservoir pad 10 into first filter element 12. In this embodiment, a reagent operable to produce a specific ligand receptor complex is uniformly impregnated throughout first filter element 12. As liquid sample emerges from reservoir pad 10, it comes in contact with the reagent impregnated in first filter element 12 where it will react to form the specific ligand receptor complex or complexes (assuming the sample contains the appropriate analyte or analytes). The use of the first filter element as a reagent delivery system obviates the need for a separate reagent addition step.

Second filter element 14, adjacent to first filter element 12 and distal to reservoir pad 10, is operable to permit passage of any specific ligand receptor complexes contained or formed in the liquid sample but to impede passage of larger components contained therein, which components may be either present in the original sample or thereafter formed, for example in first filter element 12.

Wicking membrane 16 is adjacent to second filter element 14 and distal to first filter element 12. Wicking membrane 16 has sufficient porosity and volume to absorb a substantial proportion of the sample received in reservoir pad 10 after passage through first filter element 12 and second filter element 14.

Disposed in defined zone 18 of wicking membrane 16 is an immobilized substance which is operable to bind any specific ligand receptor complexes formed and contained in the sample passing through first filter element 12 and second filter element 14.

In use, a liquid sample is applied to reservoir pad 10 of the device shown in FIG. 2. The sample migrates through first filter element 12, wherein target analytes, if present in the sample, bind to labeled reagent. The sample continues its migration through second filter element 14 wherein any unwanted components which may be present in the sample become trapped, and on into wicking membrane 16. Labeled analyte if present then binds to assay indicia zone 18 producing a visibly detectable signal.

Alternatively, immunstatus assays can be performed by applying a sample to second filter element 14 of the device shown in FIG. 2. A buffer solution is then applied to reservoir pad 10, the solution migrates through first filter element 12 reconstituting labeled reagents therein. The solution and reagents migrate through second filter element 14 wherein target analyte if present bind to the labeled reagents, and on into wicking membrane 16. Labeled analyte if present then binds to assay indicia zone 18 producing a visibly detectable signal.

Figure 3:
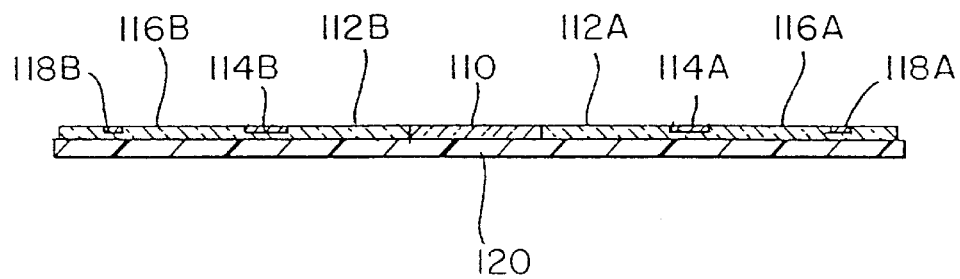
FIG. 3 is a cross sectional view of a typical bidirectional device.

Referring to FIG. 3, common reservoir pad 110, first filter elements 112A and 112B, second filter elements 114A and 114B, and wicking membranes 116A and 116B, which contain immobilized substance disposed in defined assay indicia zones 118A and 118B, are disposed on base 120. Common reservoir pad 110 has sufficient porosity and volume to receive and contain a liquid sample on which the assay is to be performed. First filter elements 112A and 112B are adjacent to and contiguous across a relatively small surface of common reservoir pad 110 with respect to the volume of pad 110 in order to meter the passage of the liquid sample from reservoir pad 110 to first filter elements 112A and 112B. Reagent operable to produce a specific ligand receptor complex is uniformly impregnated throughout first filter elements 112A and 112B. Second filter elements 114A and 114B are adjacent to first filter elements 112A and 112B respectively and distal to common reservoir pad 110, and are operable to permit passage of any specific ligand receptor complexes formed in the liquid sample but impede passage of larger components contained therein. Wicking membranes 116A and 116B have sufficient porosity and volume to absorb a substantial proportion of the sample received in common reservoir pad 110. Immobilized substance in zones 118A and 118B is operable to bind any specific ligand receptor complexes formed.

In use, a liquid sample is applied to common reservoir pad 110, the sample migrates through first filter elements 112A and 112B, wherein target analytes, if present in the sample, bind to the labeled reagents impregnated therein, through second filter elements 114A and 114B wherein any undesirable components of the fluid sample are trapped, and on into wicking membranes 116A and 116B. Target labeled analytes if present bind to assay indicia zones 118A and 118B. Thus the embodiment of FIG. 3 permits the simultaneous and independent assay of two analytes or two parallel assays for the same analyte, in each case using a single sample.

Figure 4:
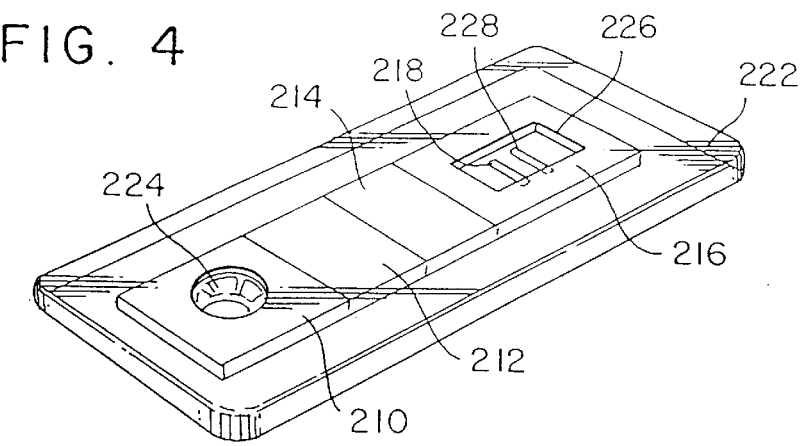
FIG. 4 is a perspective view of an assay device as depicted in FIG. 2 (shown in partial phantom lines) encased in a plastic enclosure with a single aperture.

Referring to FIG. 4, an assay device such as that shown in FIG. 2 is enclosed in casing 222. Casing 222 has aperture 224 situated directly over reservoir pad 210 and viewing window 226 situated directly over assay indicia zone 218 and assay indicia control zone 228. Window 226 can be a simple aperture or can comprise a clear material which protects zones 218 and 228 but permits visual inspection. Liquid sample is added through aperture 224 and is absorbed by reservoir pad 210. It then migrates through first filter element 212 carrying the appropriate labeled reagents through second filter element 214, in which any unwanted components of the sample are trapped, and on into wicking membrane 216 in which labeled analyte, if present, binds to assay indicia zone 218. Unbound labeled reagent binds to assay indicia control zone 228. Both indicia zones 218 and 228 can be visualized through viewing window 226.

Figure 5:
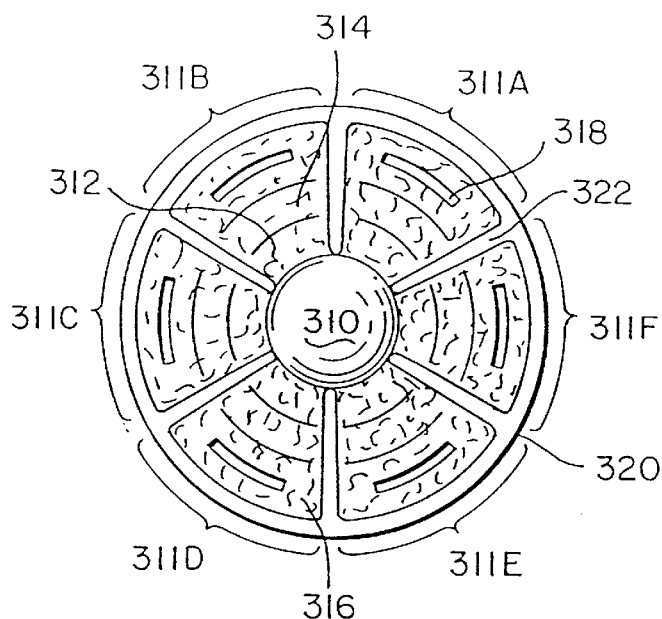
FIG. 5 is a top view of a multidirectional assay device.

Referring to FIG. 5, base 320 which is fabricated from a moisture resistant material such as plastic is segmented into a plurality of like regions 311A, 311B, 311C, 311D, 311E, and 311F by dividers 322. Each region comprising a first filter element 312, a second filter element 314, and wicking membrane 316 all disposed in base 320 between dividers 322. The same or different reagent can be deposited in each first filter element 312, permitting either parallel tests for the same analyte or a plurality of different assays on the same sample. Each wicking membrane 316 contains an immobilized substance, as appropriate for the reagent in the first filter element associated with its corresponding wicking membrane, deposited in defined assay indicia zone 318. Common reservoir pad 310 in which the sample is deposited is centrally located with respect to the plurality of regions.

In use, a fluid sample placed on reservoir pad 310 migrates simultaneously through first filter elements 312 in which target analytes, if present, bind to labeled antibodies. The sample then passes through second filter element 314 and into wicking membranes 316 in which labeled target analytes, if present, bind to the corresponding immobilized substance in assay indicia zone 318, producing a visibly detectable signal.

Figure 6:
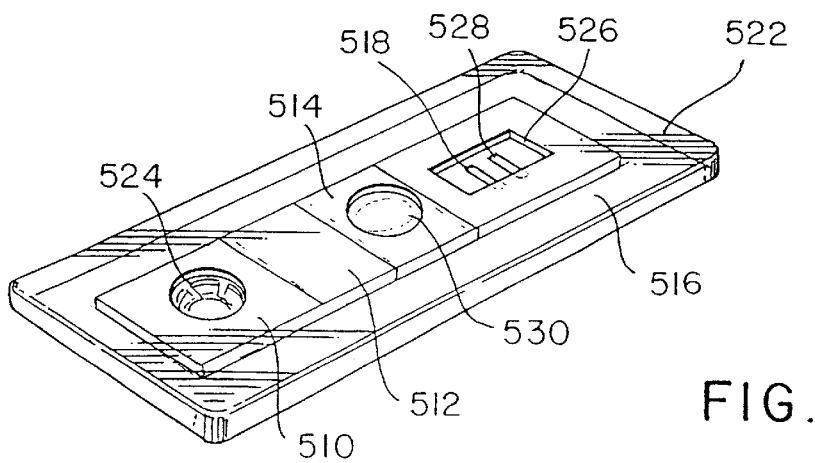
FIG. 6 is a perspective view of an assay device as depicted in FIG. 2 (shown in partial phantom lines) encased in a plastic enclosure with 2 apertures.

The embodiment shown in FIG. 6 can be used in immunstatus assays. An assay device such as that shown in FIG. 2 is enclosed in casing 522. Casing 522 has first aperture 524 situated directly over reservoir pad 510, second aperture 530 situated directly over second filter element, and viewing window 526 situated directly over assay indicia zone 518 and assay indicia control zone 528. Window 526 can be a simple aperture or can comprise a clear material which protects zones 518 and 528 but permits visual inspection. In use, a sample (as for example serum) is applied directly onto second filter element 514 through second aperture 530. A buffer solution is then applied to reservoir pad 510 through first aperture 524, the solution migrates through first filter element 512 reconstituting labeled reagents therein. The solution and reagents migrate through second filter element 514 wherein target analyte if present bind to the labeled reagents, and on into wicking membrane 516. Labeled analyte, if present, then binds to assay indicia zone 518 producing a visibly detectable signal. Unbound labeled reagent binds to assay indicia control zone 528. Both indicia zones 518 and 528 can be visualized through viewing window 526.

Regardless of the configuration, the filter elements and pads will abut or overlap one another so as to define an interface for passage of the sample. It has been found advantageous if the wicking membrane has a high area:thickness ratio whereas the filter element adjacent thereto has a relatively lower area:thickness ratio. To insure an adequate interface, it thus is advantageous to place the adjacent filter element in overlapping relation to the wicking membrane.

By incorporating at least one filter element before the assay indicia zone, an increase in sensitivity is achieved as compared to previous migration type assays. The filter, which preferably has been treated to reduce any inherent hydrophobicity, traps unwanted components in the fluid sample and allows unimpeded passage of labeled analyte. Thus, a proportionately greater amount of analyte binds to the assay indicia zone, and more accurate assay results are achieved.

Additionally by selecting a membrane with the appropriate texture and pore size, the second filter element can act as a controlled cell lysing system. For example in an immunstatus assay performed on a sample of whole blood it is advantageous to select as the second filter element a membrane which would maintain the integrity of whole blood cells while serum migrates through. This prevents the discoloration associated with blood cell lysis from spreading into the assay indicia zone.

When the device is used to perform an immunstatus assay, this additional filter element can also operate to receive samples directly. Generally, these assays are performed on samples of whole blood or serum which are spotted directly onto the filter. This is followed by the application of a buffer solution to the reservoir pad. Typical buffer solutions include, but are not limited to, phosphate buffer solution, saline, Tris-HCl, and water. Examples of antibodies which may be detected in this fashion include, but are not limited to, Acquired Immune Deficiency Syndrome, Rubella, Hepatitis, and Lymes.

Another source of assay sensitivity decline, sample flooding, also is avoided by the incorporation of the reservoir pad in the device. Thus the reservoir pad can hold a large quantity of sample which then is metered through the device as a result of the effective interface in the subsequent zones. This aspect of the invention makes it particularly suitable, for example, for home use where the device may be placed in a stream of urine without the need to measure the quantity of the sample applied to the device.

The reservoir pad, first filter element, second filter element, and wicking membrane are fashioned from any number of filter materials. Typical filter materials for use in the reservoir pad include, but are not limited to, low protein binding materials such as cellulose, polyesters, polyurethanes, and fiberglass with pore sizes in the range of 0.45–60 μm. Typical materials for use in the first filter element include, but are not limited to, cellulosic materials (e.g., Whatman paper ET31) or fiberglass with pore sizes in the range of 0.45–60 μm. Typical materials for use in the second filter element are hydrophilic materials which include, but are not limited to, polyurethane, polyacetate, cellulose, fiberglass, and nylon with pore sizes in the range of 0.45–60 μm. Typical materials for use in the wicking membrane include, but are not limited to, nylon, cellulose, polysulfone, polyvinylidene difluoride, cellulose acetate, polyurethane, fiberglass, and nitrocellulose.

The entire array of pads and membranes is attached to a solid material which provides support and unity for the device. This support can be constructed from a thin sheet of glass or plastic which has been cut to a size appropriate to include entire assay contents while providing convenience to the assay user.

Another embodiment of the present invention permits the detection of multiple analytes in a single fluid sample by the presence of more than one specific type of labeled reagent and the same number of types of corresponding immobilized reagent. The device can be set up unidirectionally with multiple labeled reagents impregnated throughout one first filter element and multiple corresponding immobilized substances defined in several assay indicia zones on the wicking membrane. In the bidirectional or multidirectional embodiment, more than one set of components such as first filter element, second filter element, and wicking membrane are associated with a common reservoir.

In each case, reagents which are incorporated in the first filter element are either dried or lyophilized onto or into the element in order to allow their reconstitution upon contact with a liquid sample. Other reagents which are useful to enhance the specificity or increase the number of ligand receptor complexes created and bound and hence increase the sensitivity of the assay device, also can be included in the filter pad, or in the first of two filter pads which also will contain the reagent. These auxiliary reagents include, but are not limited to, buffers, detergents, and anticoagulants.

By including an additional assay indicia zone to serve as a control on the wicking membrane adjacent to the first zone and distal to the second filter element, the assay device presents an internal monitor which indicates whether liquid sample has migrated throughout the entire device. Assay indicia control zones generally employ immobilized antibodies (such as anti-immunoglobins) to the labeled reagents which have been added to the analyte or incorporated into the first filter element. With reference to the embodiment of FIG. 2, for example, a liquid sample migrates through the first filter element where it reconstitutes the labeled reagent and carries it to the wicking membrane. Labeled reagent which is not bound to target analyte binds to the control assay indicia zone, creating a visibly detectable indication of test completion.

The entire assay device, whether constructed as unidirectional, bidirectional, or multidirectional, can be encased in a liquid impervious plastic. This encasing normally has an aperture over the reservoir filter in order to receive sample. The entire encasement can be transparent or a portion over the analyte detection zone can be transparent in order to observe assay results. Devices encased in plastic are especially useful and convenient for use in home diagnostic kits but other materials such as treated paper also can be employed.

Additionally, the upper surface surrounding the aperture can be curved and extended downwards so as to form cup-like receptacle which terminates at and firmly engages portion of the reservoir pad. In this way the amount of ample introduced into the device is metered and the sample cannot bypass any components of the device.

The present invention can be used with either competition assays or sandwich assays. In competition assays, an additional inclusion of a labeled antigen (which is the same as the target antigen) is included either separately or as part of the first filter element. This labeled antigen competes with antigen from the sample for binding on the detection zone.

The diagnostic devices and methods described in the present invention can be used in any ligand-receptor reactions and are especially suited for those reactions having immunochemical components such as antibodies, antigens, and haptens. In those assays in which the detection of ligand containing molecules such as antigens or haptens is desired, both the labeled reagent and substance immobilized in the assay indicia zone are ligand binding molecules. More specifically, when the ligands are antigens, both the labeled reagents and immobilized reagents will be antibodies.

The antibodies can be either monoclonal or polyclonal, the methods of producing which are well known in the art. It is preferable to use labeled monoclonal antibodies in the first filter element and polyclonal antibodies in the assay indicia zone in order to achieve maximum binding. However, any combination of monoclonal-polyclonal antibodies can be employed. In the case of home pregnancy and ovulation predictor kits, antibodies are made to human chorionic gonadotrophin and luteinizing hormones respectively and are incorporated into the device.

In those instances in which detection of a ligand binding molecule such as an antibody is desired, labeled mouse antihuman immunoglobin G is employed as the reagent which, as noted, can be incorporated in the first filter element and antigen specific to the target antibody is immobilized in the assay indicia zone. Any natural or synthetic antigen can be employed as well as polypeptide chains which have antigenic activity. Examples of antigens which can be immobilized onto the device include, but are not limited to, Rubella, Lymes, Acquired Immune Deficiency Syndrome, Hepatitis, Toxoplasmosis, Cytomegalovirus, and Epstein Barr Virus.

In assays where the simultaneous detection of more than one antibody in a single sample is desired, since the same labelled antihuman immunoglobin (reagent) recognizes and binds to all human antibodies present in the sample, it is only necessary to incorporate antigens for each target antibody in distinct indicia zones on the wicking membrane.

The labels employed in the device can be either direct or indirect. Direct labels are preferred in that they require no additional steps in order to visualize assay results. Examples of direct labels include but are not limited to, metal sols, dye sols, particulate latex, color indicators, colored matter contained in liposomes, and nonmetal sols such as a carbon sol.

In a further aspect, the invention relates to one immunochemical label which is particularly well-suited for use in the foregoing device but which can be used in other immunological assays as well, in particular, an immunochemical label in which to an immunological ligand or ligand binding molecules is linked directly or indirectly to the surface of finely particulate carbon black.

The immunological label can be diagrammatically depicted as C-L or C-X:L in which C is the finely particulate carbon black, "-" represents an adsorption linkage, L is a component containing a ligand- or ligand binding unit, X is a linking agent, and ":" represents a covalent bond.

L can consist of only the ligand- or ligand binding unit, in which case it is adsorbed directly onto the carbon. Alternatively, the ligand- or ligand binding unit can be bound to a bridging member either covalently or immunologically (herein designated by "*"). For example, the ligand- or ligand binding unit can be covalently bound to a linking agent such as glutaraldehyde which in turn is covalently bound to a proteinaceous bridging member such as bovine serum albumin (BSA) which in turn is adsorbed on the carbon. Likewise, avidin or streptoavidin can be linked through biotin to the ligand- or ligand binding molecule and the avidin or streptoavidin adsorbed on the carbon particles. Alternatively a primary antibody, serving as the ligand- or ligand binding unit is immunologically bound to a secondary antibody and the secondary antibody is adsorbed to the carbon particles. Typical structures of the C-L embodiment thus include:

C-{ligand},
C-{ligand binding molecule},
C-{protein:X:ligand},
C-{protein:X:ligand binding molecule},
C-{2-Ab*1•Ab}, and
C-{protein:X:2-Ab*1•Ab)}.

In a second embodiment, a linking agent Y is both adsorbed on the carbon particle and covalently bound to the ligand- or ligand binding unit to form a label of the general formula C-Y:L. The linking agent Y can be a single molecular species, Y', as more fully discussed below, or can be a composite such as linking agent:protein:linking agent:

C-Y':{ligand},
C-Y':{ligand binding molecule},
C-Y':protein:X:{ligand}, and
C-Y':protein:X:{ligand binding molecule}.

It will be noted that the principal difference between the two embodiments is that in the first embodiment, a ligand, ligand binding molecule, or protein (such as an antibody, bovine serum albumin, or avidin) is adsorbed on the carbon particles whereas in the second embodiment, a member of a particular class of organic compounds serving as a linking agent is adsorbed on the carbon particles and covalently bound to a ligand, ligand binding molecule, or protein.

The foregoing carbon sols can be prepared by a number of methods. The ligand and ligand binding molecules can be simply added to a suspension of the carbon particles to produce C-{ligand} and C-{ligand binding molecule} structures. In instances in which the ligand or ligand binding molecule is bound indirectly, the full, non-carbon particle structure such as {protein:X:ligand}, {protein:X:ligand binding molecule}, {2•Ab*1•Ab}, or {protein:X:2•Ab*1•Ab} can be prepared and then added to a suspension of the carbon particles for adsorption. Alternatively, a terminal portion of the non-carbon particle structure first can be adsorbed on the carbon particles and the remainder of the non-carbon particle structure then introduced chemically. For example, a protein such as bovine serum albumin, avidin, or streptoavidin can be adsorbed on the carbon particles and then linked, using for example glutaraldehyde for bovine serum albumin or biotin for avidin or streptoavidin, to the ligand or ligand binding molecule. Similarly, a 2•antibody can be adsorbed on the carbon particles and a 1•antibody then joined immunologically.

Linking reagent Y' suitable for covalently-linking ligand and ligand binding molecules such as haptens, antigens, or antibodies, or for covalently-linking protein bridging groups, include imides, azides, isothiocyanates, imidoesters, and dialdehydes, as for example, maleimide, succinimide, phenylazide, glutaraldehyde, N-hydroxysuccinimide ester, phenylisothiocyanate, 4,4'-diisothiocyanostilbene-2,2'-disulfonic acid, 4-N,N-dimethylaminoazobenzene-4'-isothiocyanate, flourescein isothiocyanate, rhodamineisothiocyanate, and the like.

As in the case of the first embodiment, the complete non-carbon particle structure, prepared by reacting the ligand (or ligand binding molecule), any bridging protein, and linking agent, can be adsorbed on the surface of the finely particulate carbon black. Alternatively, the linking reagent alone first can be adsorbed on the finely particulate carbon black and then covalently bound to the ligand, ligand binding molecule, and/or bridging protein.

In any of the above procedures, it generally is desirable to add a suspending adjuvant to the aqueous suspension of the finely particulate carbon black, as for example a polyalkylene glycol or polysaccharide. As will be seen below, similar substances subsequently are added as a protective agent after linking the immunological ligand or ligand binding molecules to the finely particulate carbon black. The amount added at this stage thus is relatively small, generally being that sufficient merely to assist in the suspension of the carbon particles.

The linking reagent then is allowed to both (i) react covalently with the immunological ligand or ligand binding molecules and (ii) be adsorbed on finely particulate carbon black, either simultaneously or sequentially. While dependent on the particular linking reagent, the linking reaction generally is conducted over several hours at pH values of from about 7.0 to about 9.5.

A variety of commercially available finely particulate carbon black materials can be used such as Monarch 1,000, 120, or 880, Vulcan XC72 or XC72R, or Regal 250R or 500R. The suitability of any particular source can be readily determined by homogenating the material in buffer and measuring the optical density.

Preferably, the finely particulate carbon black with the ligand or ligand binding molecule bound covalently or passively is treated with a polyalkylene glycol or polysaccharide protective agent to minimize hydrophobicity and maximize dispersability. Suitable materials for such coating are polyethylene glycols having a molecular weight of from about 100 to about 20,000, preferably from about 5,000 to about 12,000, and protective polysaccharides such as dextran having a molecular weight of from about 10,000 to about 500,000, preferably from about 10,000 to about 50,000. This coating can be readily achieved by contacting the linked carbon black with a 0.5% to 5% weight/volume aqueous solution of the polyethylene glycol or dextran.

In a further embodiment, the immunochemical label is treated with at least one biologically acceptable ionic or nonionic surfactant, such as long chain alkyl trimethyammonium salt, sodium deoxycholate, Tritons, Tweens, etc., in a concentration range of from about 0.01 to about 0.5%. After each such treatment, of which there can be several, with the same or different types of detergent, the immunochemical label is washed to remove excess detergent.

The resulting immunochemical label then can be suspended in an aqueous media. Such aqueous suspensions of the immunochemical label are particularly useful for the fabrication of immunoassay devices, both those of the present invention and those of other structures. Preferably the aqueous suspension includes at least one buffer in order to provide a $PK_a$ at which the labeled immunological ligand or ligand binding molecule is stable; e.g., within the range of from about 6 to about 9 and preferably from about 6.5 to about 8.5.

The following examples will serve to further typify the nature of this invention but should not be construed as a limitation on the scope thereof, which is defined solely by the appended claims.

Sensitivity Procedure

Sensitivities are determined in the following examples by preparing standard solutions of human chorionic gonadotropin in concentrations of 25 mIU/ml, 50 mIU/ml, 75 mIU/ml, and 100 mIU/ml. Samples (0.15–0.20 ml) of the standard are applied to the assay device and sensitivity determined by the ability of the device to detect a given concentration of human chorionic gonadotropin.

EXAMPLE 1

Preparation of Label

Gold sol particles are dissolved in 750 ml of distilled water which is then brought to a boil. Hydroauric acid (70 to 75 mg) is added, and boiling is continued for 5 minutes. Sodium citrate (80 mg) dissolved in 10 ml of distilled water is poured into the gold solution and the solution boiled for another 5 minutes. After allowing the solution to cool to ambient temperature, its pH is adjusted to a range close to the isoelectric point for the monoclonal antibody (determined using gel electrophoresis) made against human chorionic gonadotropic hormone. Twenty milligrams of the monoclonal antibody are added to the solution which is stirred for 2 hours at ambient temperature. Seven hundred and fifty milligrams of bovine serum albumin are added, and the solution is continuously stirred for approximately 12 hours at ambient temperature. Colloidal gold-monoclonal antibody conjugate is recovered by centrifugation at 10,000 RPM in a GSA rotor for 20 minutes, discarding the supernatant and suspending the resultant pellet in 30 ml of 1% bovine serum albumin in phosphate buffer solution (pH 7.4). The suspension is then spun down at 16,000 RPM for 15 minutes in a Sorvall SS-34 rotor. The supernatant once again is discarded and the pellet suspended in 15 ml of 1% bovine serum albumin. After a brief sonication, the suspension is filtered through a 0.2 μm filter.

B. Preparation of Device

A sample of preactivated nylon membrane (Pall Immunodyne) with a pore size of 5 μm is cut to 180 mm×25 mm size and attached to the bottom of a thin plastic plate (100 mm×180 mm) as the wicking membrane. An assay indicia zone of immobilized antibody is defined on the membrane by spraying 36 μl of a solution of 3 mg/ml sheep anti-human chorionic gonadotrophin (hCG) antibody in 0.1 M sodium phosphate buffer (pH 7.6) and 5% sucrose in a line approximately 1.5 cm from the bottom using a Camag Linomat IV. After spraying, the membrane is dried at 37° C. for 30 minutes and then treated with a solution of 2% nonfat dry milk (Carnation) and 2% sucrose in 0.1 M sodium phosphate buffer. The membrane then is washed with 2% sucrose in 0.1 sodium phosphate and allowed to stand at ambient temperature for approximately 12 hours for further drying. The base and wicking membrane can be stored in a desiccator until further processed.

Two cellulose membranes (Whatman ET31) are pretreated with a solution of 0.1 M sodium phosphate buffer (pH 7.4), 0.1% bovine serum albumin, 0.5% nonfat dry milk, 2% sucrose, and 0.05% sodium azide and then incubated for 30 minutes at ambient temperature.

The second filter element and a reservoir pad are prepared by drying the 2 pretreated cellulose membranes in a vacuum desiccator for 1 hour at ambient temperature.

The first filter element is prepared by incubating a rectangular piece of cellulose membrane (Schleicher & Schuell) measuring 5 mm×180 mm at ambient temperature for 30 minutes in a solution of colloidal gold-monoclonal anti-human chorionic gonadotropin antibody conjugate in a 0.10 M sodium phosphate buffer (pH 7.6) and 5% sucrose. The membrane then is placed on a glass plate and heat dried at 36° C. under a constant vacuum in a lyophilizer and stored dry in a desiccator until use.

The first filter element is attached adjacent to the second filter element and the second filter element is attached to the plastic base adjacent to the wicking membrane. Finally the reservoir pad is attached adjacent to the first filter element. The plastic plate then is cut into a plurality of strips 100 mm in length and 7.5 mm in width so that each contains a linear array of reservoir pad, first filter element, second filter element and wicking membrane.

EXAMPLE 2

The same procedure as Example 1B is followed except that the material used for the wicking membrane is a cellulose membrane (Schleicher & Schuell) having a pore size of 12 μm. After line-spraying with antibody, the membrane is placed in a desiccator for 24 hours to insure maximum antibody-membrane binding. The membrane then is incubated in a blocking buffer of 1% bovine serum albumin, 0.5% nonfat dry milk, 5% trehalose, 0.05% Tween 20, and 0.05% sodium azide in 0.1 M borate buffer in a pH range of 8.5 to 9. The blocked membrane is dried again in a vacuum desiccator for 1 hour and stored in a regular desiccator until incorporation into the assay device.

EXAMPLE 3

A strip is prepared according to the procedure in Example 1B.

When a stream of urine is applied to the reservoir pad a detectable signal begins to appear in the assay indicia zone after about 3 minutes. The assay sensitivity is about 50 mIU/ml.

EXAMPLE 4

A strip is prepared according to the procedure of Example 1B omitting the-first filter element and reservoir pad. The strip is inserted in a tube of 100 μl female urine which contains 10 μl of colloidal gold-monoclonal anti-human chorionic gonadotropin antibody conjugate prepared in accordance with Example 1. As the liquid migrates along the strip, a detectable signal appears in the assay indicia zone in about 2 minutes which becomes stronger by the time the liquid reached the end of the strip (about 4 minutes). The sensitivity of this assay procedure to human chorionic gonadotropin present is 25 mIU/ml.

EXAMPLE 5

A test strip is prepared substantially in accordance with the procedure in Example 1B but treating the first filter element with a anti-human chorionic gonadotropin antibody labeled as follows. A 10% suspension (0.1 ml) of commercially available colored polystyrene latex particles ranging in size from 0.1 to 0.3 μm is washed three times with distilled water by microfuge centrifugation. The final pellet is suspended in 2 ml of 0.1 M glycine hydrochloride buffer containing 1 mg of bovine serum albumin. After approximately 12 hours of incubation at ambient temperature on a rocker, the latex suspension is washed 3 times with 0.1 M sodium phosphate buffer (pH 6.8) to remove excess bovine serum albumin. The resultant suspension is brought to 2 ml with the same phosphate buffer, and 25% glutaraldehyde is added to a final concentration of 1%. The sample is incubated for 3 hours at ambient temperature and washed three more times with the same buffer. One hundred micrograms of anti-human chorionic gonadotropin antibody are added to 2 ml of the latex suspension and incubated for another 3 hours at ambient temperature. Glycine then is added to a final concentration of 2%. After an additional hour of incubation, the latex suspension is washed 3 times with the same buffer and suspended in the same buffer containing 2% bovine serum albumin. The suspension is briefly sonicated and then stored at 4° C. until use.

EXAMPLE 6

A strip is prepared according to the procedure of Example 1B omitting the first filter element and the reservoir pad. The test strip then is inserted into a test tube containing 5 μl anti-human chorionic gonadotropin antibodies labeled in accordance with the procedure in Example 5 in 100 μl of female urine. As the liquid migrates along the strip, a detectable signal appears in the assay indicia zone in about 2 minutes, which signal becomes stronger by the time the liquid reached the end of the strip (about 4 minutes). The sensitivity of this assay procedure to human chorionic gonadotropin is 25 mIU/ml.

EXAMPLE 7

Ten milligrams of Vulcan XC72 carbon particles are homogenized in 2 ml of 20 mM Tris-hydrochloride buffer (pH 6.8) containing 40 mM sodium chloride and 2% dextran 9,400. After 2 hours incubation at ambient temperature, a solution of 5 mg of flourescein isothiocyanate in 1 ml of Trishydrochloride buffer is added to the solution. The mixture is briefly sonicated and incubated for approximately 12 hours at ambient temperature. After incubation, 20 ml of 0.1 M sodium phosphate buffer (pH 7.6) in 0.1 M sodium chloride are added to the carbon solution which then is centrifuged at 4° C. at 15,000 RPM. This step is repeated three times and the resultant pellet suspended in 20 ml of phosphate buffer. After brief sonication, 3 mg of a monoclonal antibody made against human chorionic gonadotropin are added to the suspension, and the mixture incubated for 6 hours at ambient temperature. The mixture then is centrifuged three times at 15,000 RPM to remove unreacted antibody. The final pellet is suspended in 20 ml of 0.1 M Hepes buffer (pH 7.5) containing 1% bovine serum albumin, 5% sucrose, 0.1 M sodium chloride, and 0.05% sodium azide. Cetyltrimethyl ammonium bromide is added until a final concentration of 0.025% is achieved. This then is incubated for 30 minutes and centrifuged at 15,000 RPM. The resultant pellet is suspended in 20 ml of 0.1 M Hepes buffer (pH 7.5) containing 1% bovine serum albumin, 5% sucrose, 0.1M sodium chloride, and 0.05% sodium azide, sonicated briefly, and diluted with sodium deoxylate to a final concentration of 0.1%, after which it is incubated for 30 minutes at ambient temperature and recentrifuged. The pellet again is suspended in 20 ml of 0.1 M Hepes buffer (pH 7.5) containing 1% bovine serum albumin, 5% sucrose, 0.1M sodium chloride, and 0.05% sodium azide and sonicated briefly.

This carbon sol is introduced in place of colloidal gold on the first filter element of test strips prepared according to Example 1B omitting the reservoir pad. The test strips are dried in a vacuum drier for about an hour and stored in a desiccator at ambient temperature until use.

To carry out human chorionic gonadotropin or luteinizing hormone assays, 100 μl of urine sample is dispensed in a culture tube and the strip is then inserted into the tube Upon contact with the urine sample, the carbon particle-antibody conjugates immediately become solubilized and migrate toward the wicking membrane. A positive test corresponds to an intense color of the carbon black particles concentrated in the indicia. The detection limit is about 25 mIU/ml in both the human chorionic gonadotropin and luteinizing hormone assays.

EXAMPLE 8

A strip is prepared according to the procedure of Example 1B omitting the first filter element and the reservoir pad. The test strip then is inserted into a test tube containing the carbon sol labeled antibody (5 μl), and a urine sample containing human chorionic gonadotropin (100 μl) which are mixed thoroughly. A detectable signal begins to appear after about 1 minute. The sensitivity of this assay measured about 25 mIU/ml.

EXAMPLE 9

Carbon sol reagents coated with monoclonal antibodies against human chorionic gonadotropin or luteinizing hormone (5 μl per tube) are lyophilized. The tubes can be stored in a desiccator at ambient temperature until use.

To conduct human chorionic gonadotropin or luteinizing hormone assays, 100 μl of urine sample are dispersed in a culture tube containing the dried or lyophilized carbon sol. The carbon reagent immediately goes into solution upon the contact with a urine sample. A test strip prepared as in Example 1B but without the first filter element and reservoir pad and on which has been sprayed a line of sheep anti-whole human chorionic gonadotropin antibody (3 μg per strip) as the indicia then is inserted into the tube. When the migrating sample mixture reaches the indicia, a black band begins to appear if the urine sample contained human chorionic gonadotropin or luteinizing hormone. The sensitivity of the assays using the dried or lyophilized carbon reagent is about 25 mIU/ml in both cases. The dried or lyophilized carbon reagent remains active, showing the same sensitivity following storage for over a year at ambient temperature.

EXAMPLE 10

An assay device was prepared according to Example 1B eliminating the first filter element and reservoir pad and using 1 mg/ml of anti-thyroxine antibody as the line spray on the wicking membrane.

Upon insertion in a mixture of 5 μ of carbon sol linked to thyroxine (see Example 21) and 100 μl of serum (competitive assay), the control band begins to appear in about two minutes. At thyroxine (unlabeled) levels in the serum sample higher than about 60 ng/ml, no band formation occurs (faint band appears at 59 ng/ml). In contrast, to produce a band as strong as the control band in the absence of thyroxine in the serum sample, less than 10 ng/ml of thyroxine is required.

EXAMPLE 11

An assay device was prepared according to Example 1B eliminating the first filter element and reservoir pad and using 2 mg/ml of commercially available Lymes antigen (OEM Concepts) as the line spray on the wicking membrane.

When the reservoir end of the device is dipped into a mixture of 100 μl of human serum and 5 μl of carbon particles labeled with flourescein isothiocyanate-conjugated goat anti-human Immunoglobin G (see Example 21), a detectable signal appears in about 4 minutes if the sample is seropositive.

EXAMPLE 12

An assay device was prepared according to Example 11. Ten microliters of human serum was spotted onto the second filter element. The device was inserted into a tube containing a 100 μl suspension of carbon particles (5 μl) labeled with flourescein isothiocyanate-conjugated goat anti-human Immunoglobin G (see Example 21) in 20 mM ethylenediaminetetraacetate. A detectable signal appears in 5 minutes if the sample is seropositive.

EXAMPLE 13

An assay device was prepared according to Example 11 except 2 mg/ml of Rubella antigen (Viral Antigens, Inc.) was line-sprayed on the wicking membrane.

When the reservoir pad is contacted with 100 μl of human serum and 5 μl carbon particles labeled with flourescein isothiocyanate conjugated goat anti-human Immunoglobin G (see Example 21), a detectable signal appears in about 2 minutes if the sample is seropositive.

EXAMPLE 14

An assay device was prepared according to Example 13. Then microliters of serum was spotted on the second filter element and the device was inserted into a tube containing a 100 μl suspension of carbon particles labeled with flourescein isothiocyanate conjugated goat anti-human Immunoglobin G (see Example 21) in 20 mM ethylenediaminetetraacetate.

A detectable signal appears in about 3 minutes if the sample is seropositive.

EXAMPLE 15

An assay device was prepared according to Example 11 and an additional line of Rubella antigen was sprayed approximately 7 mm from and parallel to the line of lyme antigen.

A Rubella seropositive sample (10 µl) was spotted on the second filter element. The device was inserted into a tube containing a 100 µl suspension of carbon particles (10 µl) labeled with flourescein isothiocyanate conjugated goat anti-human Immunoglobin G (see Example 21) in 20 mM ethylenediamine tetraacetate.

A detectable signal appeared in about 5 minutes along the line of Rubella antigen.

EXAMPLE 16

The procedure in Example 15 was followed except that a Rubella and Lyme seropositive sample (20 µl) was spotted on the membrane. Two detectable signals began to appear in about 5 minutes.

EXAMPLE 17

The suitability of different carbon materials for preparation of the carbon sols and buffers for the same can be readily determined by the following techniques.

A. Mixtures of 5 mg of different carbon black (Monarch 1,000, Monarch 880, Monarch 120, Regal 250R, Regal 500R, Vulcan XC72R, and Vulcan XC72, all obtained from Cabot) and 100 µl of 2% polyethylene glycol (6,000–8,000) are ground for 5 min. and diluted up to 10 ml with phosphate saline buffer containing 2 mg of a monoclonal antibody made against human chorionic gonadotropin. After a brief sonication to disperse the carbon particles in the monoclonal antibody solution, the mixtures are incubated for 6 hours at ambient temperature with stirring. At the end of the incubation, the sample is washed three times by centrifugation to remove any excess antibody. Each centrifugation is carried out at 15,000 RPM for 20 min. using 10 ml of phosphate buffer solution. The final pellet is suspended in 10 ml of 3% phosphate buffer solution and sonicated briefly to ensure complete dispersion of the carbon particles.

For human chorionic gonadotropin assay, 20 µl of the carbon sol and 200 µl of urine sample are dispersed and mixed well in a culture tube (10×75 mm). The mixture is then allowed to migrate into a strip of Whatman paper (31ET) measuring 5 mm in width and 100 mm in height, line-sprayed with sheep anti-human chorionic gonadotropin antibody and blocked with 1% bovine serum albumin in phosphate buffer solution (pH 7.4).

Vulcan XC72 appears to give the best signal-to-noise ratio at 200 mIU/ml human chorionic gonadotropin. Similar results are obtained with Vulcan XC72R, but the positive signal is slightly lower.

B. Five milligrams of the same carbon blacks are suspended in 2 ml of 20 mM Tris-HC1 buffer (pH 6.8) containing 40 mm sodium chloride and 2% (w/v) dextran 9,400 by homogenization. After 2 hours of incubation at ambient temperature, 1 ml of 3% bovine serum albumin solution is added to the homogenized carbon suspension. The mixture is sonicated briefly and incubated further for approximately 12 hours at ambient temperature. At the end of the incubation, 5 µl of the mixture is dispensed in a cuvette containing 1 ml of distilled water. Absorbency at 700 nm is measured for each sample. The results are as follows:

| Source of Carbon Black | OD at 700 nm |
| --- | --- |
| Monarch 1,000 | 0.2333 |
| Monarch 880 | 0.3129 |
| Vulcan XC72R | 0.6878 |
| Vulcan XC72 | 0.7428 |
| Monarch 120 | 0.6225 |
| Regal 250R | 0.3567 |
| Regal 500R | 0.4372 |

C. Vulcan XC72 carbon black is suspended in several buffer solutions having different pH. Five milligrams of Vulcan XC72 carbon particles are homogenized in 2 ml of different buffer solutions containing 2% dextran 9,400 and incubated for 2 hours at ambient temperature. After the incubation, 5 µl of each homogenate are added to 1 ml of distilled water. One milliliter of 3% bovine serum albumin in the same buffer is added to the mixture which is then sonicated and incubated for approximately 12 hours at ambient temperature. At the end of the incubation, 5 µl of the mixture are suspended in 1 ml of distilled water and absorbency is measured at 700 nm. The results are as follows:

| Buffers | Ionic Strength | pH | OD at 700 nm Dextran | OD at 700 nm Bovine Serum Albumin |
| --- | --- | --- | --- | --- |
| sodium phosphate | 0.1M | 6.0 | 0.3335 | 0.6030 |
| sodium phosphate | 0.1M | 6.8 | 0.5142 | 0.7462 |
| Tris-HCl | 0.02M | 6.8 | 0.6277 | 0.8452 |
| sodium phosphate | 0.003M | 7.0 | 0.4722 | 0.5389 |
| sodium phosphate | 0.1M | 7.6 | 0.4348 | 0.6100 |
| Tris-HCl | 0.02M | 8.0 | 0.6479 | 0.5220 |
| glycine-HCl | 0.1M | 8.3 | 0.4666 | 0.5197 |
| Tris-citrate | 0.1M | 8.6 | 0.4284 | 0.4933 |

As can be seen, buffer solutions having pH values of about 6.8 to 8 are particularly good for the dispersion of carbon particles.

EXAMPLE 18

To a mixture of 1 mg of anti-human chorionic gonadotropin antibody in 1 ml of 0.3 M borate buffer (pH 9.0) are added with stirring 50 µg of flourescein isothiocyanate. Stirring is continued for one hour and the mixture is then passed over a Sephadex G-25 column to remove unreacted isothiocyanate and other unwanted materials. The ratio of antibody:isothiocyanate was approximately 1:3. To an aqueous suspension of 1 mg of carbon black (Vulcan 72) is added 0.5 mg of the antibody conjugate. The mixture is sonicated, incubated for about 12 hours at ambient temperatures, and subjected to centrifugation three times. The final pellet, suspended in a buffer such as described in Example 12, can be stored at 4° C. until use.

Similar products can be obtained utilizing anti-luteinizing hormone, goat anti-human Immunoglobin G, and Immunoglobin M antibodies.

EXAMPLE 19

To 10 ml of an aqueous suspension of 5 mg of carbon black (Vulcan 72) is added 200 µl of goat anti-mouse antiserum. The mixture is sonicated and incubated for about 12 hours at ambient temperatures. There then is added 1 mg of anti-human chorionic gonadotropin antibody and this mixture is incubated for two hours at ambient temperatures and subjected to centrifugation three times. The final pellet, suspended in a buffer such as described in Example 12, can be stored at 4° C. until use.

EXAMPLE 20

To a suspension of 5 mg of carbon black in 10 ml of phosphate buffer solution (PBS) are added 2 mg of avidin. After incubation for two hours at ambient temperature, 5 ml of 3% bovine serum albumin in PBS are added. After standing for two hours, 0.5 mg of biotinylated anti-human chorionic gonadotropin in 1% bovine serum albumin in PBS is added. After an additional one hour incubation, the mixture is subjected to centrifugation three times. The final pellet, suspended in a buffer such as described in Example 12 and then briefly sonicated, can be stored at 4° C. until use.

EXAMPLE 21

Ten milligrams of Vulcan XC72 carbon particles are homogenized in 2 ml of 20 mM Tris-hydrochloride buffer (pH 6.8) containing 40 mM sodium chloride and 2% dextran 9,400. After 2 hours incubation at ambient temperature; a solution of 5 mg of flourescein isothiocyanate in 1 ml of Tris-hydrochloride buffer is added to the solution. The mixture is briefly sonicated and incubated for approximately 12 hours at ambient temperature. After incubation, 20 ml of 0.1 M sodium phosphate buffer (pH 7.6) in 0.1 M sodium chloride are added to the carbon solution which then is centrifuged at 4° C. at 15,000 RPM. This step is repeated three times and the resultant pellet suspended in 20 ml of phosphate buffer.

Two milligrams of bovine serum albumin are added to 2 ml of the above suspension and the mixture incubated for six hours and then subjected to centrifugation three times. Excess glutaraldehyde (1%) is added and after incubation for three hours at ambient temperature removed by centrifugation. A solution of 10 $\mu$g of thyroxine in sufficient dimethylformamide is added and this mixture is incubated for three hours at ambient temperature and then subjected to centrifugation three times. The final pellet, suspended in a buffer such as described in Example 12 and then briefly sonicated, can be stored at 4° C. until use.

What is claimed is:

1. An immunochemical assay device comprising:
   a base member;
   a filter element at least partially disposed on a first portion of said base member, said filter element having located thereon a labeled immunochemical component capable of binding to an analyte of interest in the sample to form an immuno-complex; and
   a wicking membrane at least partially disposed on a second portion of said base member, said wicking membrane having at least one immobilized substance located thereon in at least one assay indicia zone, said immobilized substance being operable to bind said immuno-complex contained in the sample,
   wherein said wicking membrane is longer than said filter element, said wicking membrane and said filter element are separate components, said wicking membrane abuts or overlaps said filter element such that an interface is defined there between for passage of the sample from the filter element downstream to said wicking membrane, and said second portion of said base member extends from said first portion to at least said assay indicia zone on said wicking membrane.

2. The device according to claim 1, wherein:
   said filter element and said wicking membrane are formed of two different materials.

3. The device according to claim 1, wherein:
   said filter element is formed from a first material having a first pore size,
   said wicking membrane is formed from a second material having a second pore size, and
   said pore size and said second pore size are different.

4. The device according to claim 3, wherein:
   said first pore size is larger than said second pore size.

5. An immunochemical assay device comprising:
   a base member;
   a first pad at least partially disposed on a first portion of said base member, said first pad having located thereon a direct labeled immunochemical component capable of binding to an analyte of interest in the sample to form an immuno-complex; and
   a wicking membrane at least partially disposed on a second portion of said base member, said wicking membrane having at least one immobilized substance located thereon in at least one assay indicia zone, said immobilized substance being operable to bind to a specific immuno-complex contained in the sample,
   wherein said wicking membrane is longer than said first pad, said wicking membrane and said first pad are separate components and said wicking membrane abuts or overlaps said first pad such that an interface is defined there between for passage of the sample from the first pad downstream to said wicking membrane.

6. An immunochemical assay device comprising:
   a base member;
   a first pad at least partially disposed on a first portion of said base member, said first pad having located thereon a direct labeled immunochemical component capable of binding to an analyte of interest in the sample to form an immuno-complex; and
   a wicking membrane at least partially disposed on a second portion of said base member, said wicking membrane having at least one immobilized substance located thereon in at least one assay indicia zone, said immobilized substance being operable to bind unbound labeled immunochemical component contained in the sample,
   wherein said wicking membrane is longer than said first pad, said wicking membrane and said first pad are separate components and said wicking membrane abuts or overlaps said first pad such that an interface is defined there between for passage of the sample from the first pad downstream to said wicking membrane.

7. An immunochemical assay device comprising:
   a base member;
   a first pad at least partially disposed on a first portion of said base member, said first pad having located thereon a direct labeled immunochemical component capable of competing with an analyte of interest in the sample; and
   a wicking membrane at least partially disposed on a second portion of said base member, said wicking membrane having at least one immobilized substance located thereon in at least one assay indicia zone, said immobilized substance being operable to bind said labeled immunochemical component or analyte contained in the sample,
   wherein said wicking membrane is longer than said first pad, said wicking membrane and said first pad are separate components and said wicking membrane abuts or overlaps said first pad such that an interface is defined there between for passage of the sample from the first pad downstream to said wicking membrane.

8. The device according to claim 5, 6, or 7, wherein:
said first pad and said wicking membrane are formed of two different materials.

9. The device according to claim 5, 6, or 7, wherein:
said first pad is formed from a first material having a first pore size,
said wicking membrane is formed from a second material having a second pore size; and
said first pore size and said second pore size are different.

10. The device according to claim 9, wherein:
said first pore size is larger than said second pore size.

11. An immunochemical assay device comprising:
a base member;
a filter element at least partially disposed on a first portion of said base member, said filter element having located thereron a labeled immunochemical component capable of binding to an analyte of interest in the sample to form an immuno-complex; and
a wicking membrane at least partially disposed on a second portion of said base member, said wicking member having at least one immobilized substance located thereon in at least one assay indicia zone, said immobilized substance being operable to bind said immuno-complex contained in the sample,
wherein said wicking membrane is longer than said filter element, said wicking membrane and said filter element are separate components, said filter element abuts or overlaps said wicking membrane such that an interference is defined there between for passage of the sample from the filter element downstream to said wicking membrane, and said second portion of said base member extends from said first portion to at least said assay indicia zone on said wicking membrane.

12. The device according to claim 11, wherein:
said filter element and said wicking membrane are formed of two different materials.

13. The device according to claim 11, wherein:
said filter element is formed from a first material having a first pore size,
said wicking membrane is formed from a second material having a second pore size, and
said first pore size and said second pore size are different.

14. The device according to claim 13, wherein:
said first pore size is larger than said second pore size.

15. An immunochemical assay device comprising:
a base member;
a first pad at least partially disposed on a first portion of said base member, said first pad having located thereon a direct labeled immunochemical component capable of binding to an analyte of interest in the sample to form an immuno-complex; and
a wicking membrane at least partially disposed on a second portion of said base member, said wicking membrane having at least one immobilized substance located thereon in at least one assay indicia zone, said immobilized substance being operable to bind to a specific immuno-complex contained in the sample,
wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

16. An immunochemical assay device comprising:
a base member;
a first pad at least partially disposed on a first portion of said base member, said first pad having located thereon a direct labeled immunochemical component capable of binding to an analyte of interest in the sample to form an immuno-complex; and
a wicking membrane at least partially disposed on a second portion of said base member, said wicking membrane having at least one immobilized substance located thereon in at least one assay indicia zone, said immobilized substance being operable to bind unbound labeled immunochemical component contained in the sample,
wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

17. An immunochemical assay device comprising:
a base member;
at first pad at least partially disposed on a first portion of said base member, said first pad having located thereon a direct labeled immunochemical component capable of competing with an analyte of interest in the sample; and
a wicking membrane at least partially disposed on a second portion of said base member, said wicking membrane having at least one immobilized substance located thereon in at least one assay indicia zone, said immobilized substance being operable to bind said labeled immunochemical component or analyte contained in the sample,
wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

18. An immunochemical assay device comprising:
a base member;
a first pad at least partially disposed on a first portion of said base member, said first pad having located thereon a direct labeled immunochemical component capable of binding to an analyte of interest in the sample to form an immuno-complex; and
a wicking membrane at least partially disposed on a second portion of said base member, said wicking membrane having at least one immobilized substance located thereon in at least one assay indicia zone, said immobilized substance being operable to bind to a specific immuno-complex contained in the sample,
wherein said wicking membrane is longer than said first pad and said wicking membrane and said first pad are separate components.

19. An immunochemical assay device comprising:
a base member;
a first pad at least partially disposed on a first portion of said base member, said first pad having located thereon a direct labeled immunochemical component capable of binding to an analyte of interest in the sample to form an immuno-complex; and
a wicking membrane at least partially disposed on a second portion of said base member, said wicking membrane having at least one immobilized substance located thereon in at least one assay indicia zone, said immobilized substance being operable to bind unbound labeled immunochemical component contained in the sample,
wherein said wicking membrane is longer than said first pad and said wicking membrane and said first pad are separate components.

20. An immunochemical assay device comprising:

a base member;

a first pad at least partially disposed on a first portion of said base member, said first pad having located thereon a direct labeled immunochemical component capable of competing with an analyte of interest in the sample; and a wicking membrane at least partially disposed on a second portion of said base member, said wicking membrane having at least one immobilized substance located thereon in at least one assay indicia zone, said immobilized substance being operable to bind said labeled immunochemical component or analyte contained in the sample, wherein said wicking membrane is longer than said first pad and said wicking membrane and said first pad are separate components.

21. An immunochemical assay device comprising:

a base member;

a first pad at least partially disposed on a first portion of said base member, said first pad having located thereon a labeled immunochemical component capable of binding to an analyte of interest in the sample to form an immuno-complex; and a wicking membrane at least partially disposed on a second portion of said base member, said wicking membrane having at least one immobilized substance located thereon in at least one assay indicia zone, said immobilized substance being operable to bind to a specific immuno-complex contained in the sample, wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

22. An immunochemical assay device comprising:

a base member;

a first pad at least partially disposed on a first portion of said base member, said first pad having located thereon a labeled immunochemical component capable of binding to an analyte of interest in the sample to form an immuno-complex; and a wicking membrane at least partially disposed on a second portion of said base member, said wicking membrane having at least one immobilized substance located thereon in at least one assay indicia zone, said immobilized substance being operable to bind unbound labeled immunochemical component contained in the sample, wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

23. An immunochemical assay device comprising:

a base member;

a first pad at least partially disposed on a first portion of said base member, said first pad having located thereon a labeled immunochemical component capable of competing with an analyte of interest in the sample; and a wicking membrane at least partially disposed on a second portion of said base member, said wicking membrane having at least one immobilized substance located thereon in at least one assay indicia zone, said immobilized substance being operable to bind said labeled immunochemical component or analyte contained in the sample, wherein said wicking membrane is longer than said first pad, said wicking membrane and said first pad are separate components and said first pad abuts or overlaps said wicking membrane such that an interface is defined there between for passage of the sample from the first pad downstream to said wicking membrane.

24. An immunochemical assay device comprising:

a base member a first pad at least partially disposed on a first portion of said base member, said first pad having located thereon a labeled immunochemical component capable of binding to an analyte of interest in the sample to form an immuno-complex; and a wicking membrane at least partially disposed on a second portion of said base member, said wicking membrane having at least one immobilized substance located thereon in at least one assay indicia zone, said immobilized substance being operable to bind to a specific immuno-complex contained in the sample, wherein said wicking membrane is longer than said first pad and said wicking membrane and said first pad are separate components.

25. An immunochemical assay device comprising:

a base member;

a first pad at least partially disposed on a first portion of said base member, said first pad having located thereon a labeled immunochemical component capable of binding to an analyte of interest in the sample to form an immuno-complex; and a wicking membrane at least partially disposed on a second portion of said base member, said wicking membrane having at least one immobilized substance located thereon in at least one assay indicia zone, said immobilized substance being operable to bind unbound labeled immunochemical component contained in the sample, wherein said wicking membrane is longer than said first pad and said wicking membrane and said first pad are separate components.

26. An immunochemical assay device comprising:

a base member;

a first pad at least partially disposed on a first portion of said base member, said first pad having located thereon a labeled immunochemical component capable of competing with an analyte of interest in the sample; and a wicking membrane at least partially disposed on a second portion of said base member, said wicking membrane having at least one immobilized substance located thereon in at least one assay indicia zone, said immobilized substance being operable to bind said labeled immunochemical component or analyte contained in the sample, wherein said wicking membrane is longer than said first pad and said wicking membrane and said first pad are separate components.

* * * * *